(12) United States Patent
Deuchar et al.

(10) Patent No.: US 10,278,642 B2
(45) Date of Patent: May 7, 2019

(54) METHODS OF ASSESSING METABOLIC FUNCTION

(71) Applicant: Aurum Biosciences Limited, Glasgow (GB)

(72) Inventors: Graeme Deuchar, Glasgow (GB); Celestine Santosh, Glasgow (GB)

(73) Assignee: Aurum Biosciences Limited, Glasgow (GB)

( * ) Notice: Subject to any disclaimer, the term of this patent is extended or adjusted under 35 U.S.C. 154(b) by 632 days.

(21) Appl. No.: 14/647,628

(22) PCT Filed: Nov. 27, 2013

(86) PCT No.: PCT/GB2013/053130
§ 371 (c)(1),
(2) Date: May 27, 2015

(87) PCT Pub. No.: WO2014/083331
PCT Pub. Date: Jun. 5, 2014

(65) Prior Publication Data
US 2015/0313540 A1    Nov. 5, 2015

(30) Foreign Application Priority Data
Nov. 27, 2012   (GB) .................................. 1221305.4

(51) Int. Cl.
*A61B 5/05*   (2006.01)
*A61B 5/00*   (2006.01)
(Continued)

(52) U.S. Cl.
CPC .......... *A61B 5/4866* (2013.01); *A61B 5/0042* (2013.01); *A61B 5/055* (2013.01);
(Continued)

(58) Field of Classification Search
CPC . A61B 5/4866; A61B 5/7246; A61B 5/14542; A61B 5/0042; A61B 5/055;
(Continued)

(56) References Cited

U.S. PATENT DOCUMENTS

| 5,639,473 A | 6/1997 | Grinstaff et al. | |
|---|---|---|---|
| 2009/0246138 A1* | 10/2009 | Santosh ................. | A61B 5/055 424/9.2 |
| 2011/0035198 A1* | 2/2011 | McGrath ................ | A61B 5/055 703/2 |

FOREIGN PATENT DOCUMENTS

| WO | WO-2008023176 A1 | 2/2008 |
|---|---|---|
| WO | WO-2011027165 A1 | 3/2011 |

OTHER PUBLICATIONS

Communication from Examining Division in EP Application No. 13810984.8 dated Jan. 24, 2017, 5 pages.
(Continued)

*Primary Examiner* — Sanjay Cattungal
(74) *Attorney, Agent, or Firm* — Marshall, Gerstein & Borun LLP (57) ABSTRACT

The present invention relates to improved methods for determining metabolic function in tissues of an animal. In particular, the invention relates to methods for determining the penumbra in ischaemic tissues using MRI techniques in association with hyperoxic conditions and an oxygen carrier. The invention also relates to systems adapted to perform the methods.

28 Claims, 3 Drawing Sheets

(51) Int. Cl.
| | |
|---|---|
| A61M 16/10 | (2006.01) |
| A61B 5/145 | (2006.01) |
| G01R 33/50 | (2006.01) |
| A61D 7/00 | (2006.01) |
| A61B 5/055 | (2006.01) |

(52) U.S. Cl.
CPC ........ *A61B 5/14542* (2013.01); *A61B 5/7246* (2013.01); *A61D 7/00* (2013.01); *A61M 16/1005* (2014.02); *G01R 33/50* (2013.01); A61B 2576/026 (2013.01); A61M 2202/0208 (2013.01)

(58) Field of Classification Search
CPC ............... A61B 2576/026; A61D 7/00; A61M 16/1005; A61M 2202/0208; G01R 33/50
See application file for complete search history.

(56) References Cited

OTHER PUBLICATIONS

International Preliminary Report on Patentability and Written Opinion in International Application No. PCT/GB2013/053130 dated Jun. 2, 2015, 7 pages.
Database Compendex Engineering Information Inc., New York, NY, 1994, Keipert, et al. "Influence of perflubron emulsion particle size on blood half-life and febrile response in rats", XP002720098.
Heiss et al., "Progressive Derangement of Periinfarct Viable Tissue in Ischemic Stroke", Journal of Cerebral Blood Flow and Metabolism, vol. 12, 1992, pp. 193-203.
"Thresholds in Cerebral Ischemia—The Ischemic Penumbra", Stroke, A Journal of Cerebral Circulation, American Heart Association, vol. 12, No. 6, Nov.-Dec. 1981, pp. 723-725.
Law et al., "The Physiology of Oxygen Delivery", Update in Anaesthesia, www.worldanaesthesia.org 2008, pp. 20-25.
Pauling et al., "The Magnetic Properties and Structure of Hemoglobin, Oxyhemoglobin and Carbonmonoxyhemoglobin", Proc. N.A. S., vol. 22, Gates Chemical Laboratory, California Institute of Technology, 1936, pp. 210-216.
Ogawa et al., "Brain Magnetic Resonance Imaging With Contrast Dependent on Blood Oxygenation", Proc. Natl. Acad. Sci., vol. 87, Dec. 1990, pp. 9868-9872.
Heiss et al., "Which Targets are Relevant for Therapy of Acute Ischemic Stroke?", http://stroke.ahajournals.org/, downloaded from the internet on Dec. 1, 2015, pp. 1486-1489.
Schaller et al., "Cerebral Ischemia and Reperfusion: The Pathophysiologic Concept as a Basis for Clinical Therapy", Journal of Cerebral Blood Flow & Metabolism, vol. 24, 2004, pp. 351-371.
Hakim, "The Cerebral Ischemic Penumbra", Le Journal Canadien Des Sciences Neurologiques, vol. 14, No. 4, Nov. 1987, pp. 557-559.
Leão, "Spreading Depression of Activity in the Cerebral Cortex", from a Thesis submitted Oct. 1943, 1 page.
Branston et al., "Extracellular Potassium Activity, Evoked Potential and Tissue Blood Flow", Journal of the Neurological Sciences, vol. 32, 1977, pp. 305-321.
Fabricius et al., "Cortical Spreading Depression and Peri-Infarct Depolarization in Acutely Injured Human Cerebral Cortex", Brain, 129, 2006, pp. 778-790.
Wolf et al., "Noninvasive Near Infrared Spectroscopy Monitoring of Regional Cerebral Blood Oxygenation Changes During Peri-Infarct Depolarizations in Focal Cerebral ischemia in the Rat", Journal of Cerebral Blood Flow and Metabolism, vol. 17, 1997, pp. 950-954.
Fenstermacher et al., "Serial Proton Magnetic Resonance Spectroscopy of Ischemic Brain Injury in Humans", Investigative Radiology, Sep. 1990, vol. 25, pp. 1034-1039.
Houkin, "Proton and Phosphorus-31 Nuclear Magnetic Resonance Spectroscopy in Experimental Cerebral Infarction in Rats", Department of Neurosurgery, Hokkaido University, School of Medicine, Hokkaido Igaku Zasshi 1990, 65(6), Nov. 1990, pp. 595-603.
Jean-Claude Baron, "Mapping the Ischaemic Penumbra with PET: a New Approach", Editorial, Oxford University Press 2001, 3 pages.
Marchal et al., "Prolonged Persistence of Substantial Volumes of Potentially Viable Brain Tissue After Stroke", American Heart Association, 1996, 12 pages.
Guadagno et al., "The Diffusion-Weighted Lesion in Acute Stroke: Heterogeneous Patterns of Flow/Metabolism Uncoupling as Assessed by Quantitative Positron Emission Tomography", Cerebrovasc Dis. vol. 19, 2005, pp. 239-246.
Tracey Baskerville, et al., "Influence of 100% and 40% oxygen on penumbral blood flow, oxygen level, and $T^*_2$-weighted MRI in a rat stroke model", Journal of Cerebral Blood Flow and Metabolism: Official Journal of the International Society of Cerebral Blood Flow and Metabolism, vol. 31, No. 8, Aug. 2011.
Database Compendex Engineering Information Inc., New York, NY, 1994, Keipert, et al. "Influence of perflubron emulsion particle size on blood half-life and debrile response in rats", XP002720098.
International Search Report from International Application No. PCT/GB2013/053130 dated Mar. 5, 2014.

\* cited by examiner

METHODS OF ASSESSING METABOLIC FUNCTION

FIELD OF THE INVENTION

The present invention relates to improved methods for determining metabolic function in tissues of an animal. In particular, the invention relates to methods for determining the penumbra in ischaemic tissues. The invention also relates to systems adapted to perform the methods.

BACKGROUND TO THE INVENTION

MRI (Magnetic Resonance Imaging) is an imaging technique based on the phenomenon of nuclear magnetic resonance. Functional magnetic resonance imaging (fMRI) is a variation of magnetic resonance imaging which can be used for analysis and evaluation of brain function. Brain function consumes a large amount of energy and this is provided almost exclusively by glucose oxidation. Brain function is therefore dependent on glucose and oxygen, which is provided by the circulating blood. These characteristics have been exploited to study brain function in vivo.

The technique of functional MRI (fMRI) is based on the physiological principle that when nerve cells are active they consume oxygen carried by haemoglobin in red blood cells. In response the small blood vessels in the region dilate and blood flow is increased to the regions of increased neural activity. This delivers a large amount of oxygenated blood to the region.

The oxygen carried by the blood is bound to the protein haemoglobin. The magnetic properties of haemoglobin, oxygenated haemoglobin (oxyhaemoglobin) and deoxygenated haemoglobin (deoxyhaemoglobin) were demonstrated as long ago as 1936. The magnetic resonance (MR) signal of blood is modulated by the ratio of oxyhaemoglobin and deoxyhaemoglobin. Many decades later this property was shown in vivo and was termed "Blood Oxygen Level Dependent" (BOLD) contrast. In BOLD fMRI changes in blood oxygen level are observed as signal changes from a baseline.

In the BOLD method the fact that oxyhaemoglobin and deoxyhaemoglobin are magnetically different is exploited. Oxyhaemoglobin is diamagnetic whereas deoxyhaemoglobin is paramagnetic. As deoxyhaemoglobin is paramagnetic, it alters the $T_2^*$ weighted magnetic resonance image signal. Thus, deoxyhaemoglobin is sometimes referred to as an endogenous contrast enhancing agent, and serves as the source of the signal for fMRI. The fMRI technique has been widely used for more than a decade to understand brain function by activating different brain areas by appropriate stimuli using different paradigms.

Upon neural activity, oxygen consumption is increased. This results in a corresponding reduction in deoxyhaemoglobin as the increase in blood flow brings more oxyhaemoglobin into the area without an increase of similar magnitude in oxygen consumption. This causes a small change in the magnetic field, and thus the MRI signal, in the active region. As deoxyhaemoglobin is paramagnetic, and the water molecules around the red blood cells are affected by the resulting local magnetic field distortions, a reduction of the $T_2^*$ magnetic resonance image signal value is observed. Despite the existence of such valuable imaging methods, there remains a need for improved techniques to permit better understanding of physiology, particularly to recognize metabolic dysfunction before it is too late for an appropriate intervention or procedure to be applied.

The concept of the ischaemic penumbra is now more than 30 years old. Following occlusion of a brain artery some of the brain tissues supplied by the vessel perish due to hypoxia/anoxia. This happens due to the inability of cells to produce ATP (energy) leading to cell dysfunction and then cell death. However, some tissues have a capability to recover with appropriate treatment. Astrup (Astrup et al., 1981) first defined ischemic penumbra in 1981 as perfused brain tissue at a level within the thresholds of functional impairment and morphological integrity, which has the capacity to recover if perfusion is improved. Therefore any technique demonstrative of active metabolism within the affected tissues would, at least in theory, also be able to detect the penumbra.

Stroke can result in complete arterial occlusion which leads to the failure of neuronal electrical activity within seconds and then to the deterioration of the energy state within a few minutes. If this lack of energy lasts for longer than 5-10 minutes, irreversible cell damage occurs. The 'penumbra' following stroke relates to brain tissues where blood flow is reduced enough to cause hypoxia affecting neuronal function but where energy metabolism is preserved preventing rapid cell death. This penumbra tissue has the potential to respond to appropriate treatment and recover normal neuronal function. The penumbra surrounds the core of the infarct where severely ischaemic tissue suffers complete energy failure resulting in irreversible injury. Therefore in order to accurately identify the penumbra following ischaemia, it would be necessary to demonstrate hypoperfused brain tissues that have maintained metabolic and electrical activity.

WO 2008/023176 discloses methods of imaging metabolic function. These methods involve contrast imaging techniques of the "BOLD" type but adapted by use together with an oxygen challenge to provide imaging for the assessment of the metabolic responses of tissue over a period of time.

WO 2011/027165 discloses the use of lactate levels in determining the penumbra.

The present invention is based upon the surprising observation that administering a bolus of oxygen via an oxygen carrier (e.g. an intravenous dose of a PFC or other oxygen carrying liquid) allows the penumbra to be readily and accurately determined using MRI.

SUMMARY OF THE INVENTION

According to an aspect of the present invention, there is provided a method of imaging metabolic function in a target region of an animal using magnetic resonance imaging, the method comprising the steps of:
  i) administering oxygen to said animal such that the animal is hyperoxic;
  ii) obtaining a baseline measurement of a signal indicative of deoxyhaemoglobin level in a target region of the animal;
  iii) administering an oxygen carrier to the subject such that it will enter the blood supply of the animal;
  iv) obtaining at least a second measurement of a signal indicative of deoxyhaemoglobin level in the target region of the animal following administration of the oxygen carrier;
  v) comparing said baseline and second measurements to obtain data relating to the relative amounts of deoxyhaemoglobin present in said target region in the baseline measurement and following administration of the oxygen carrier, and correlating said data to the metabolic function of the target region.

In step v) the observation of a change in the signal in the target region which is indicative of an increase in deoxyhaemoglobin levels is indicative of the penumbra. The increase in deoxyhaemoglobin level will typically then be followed by a return to (or near to) the baseline level obtained in step ii). It is a characteristic of the present invention that changes in the signal are substantially restricted to the penumbra, without any significant changes being observed in the ischaemic core or tissues surrounding the penumbra.

The change in signal may be observed across the whole of the target region or may be observed only in a part of the region.

Preferably the signal indicative of deoxyhaemoglobin level is a $T_2^*$ signal. Other signals which allow determination of deoxyhaemoglobin levels could of course be used.

In a preferred embodiment step iv) of the method comprises obtaining a plurality of measurements over a suitable period of time. These measurements are taken over a period of time sufficient to allow the observation of changes in the levels of deoxyhaemoglobin in the target region following administration of the oxygen carrier. The period of time may be from about 5 seconds to about 10 minutes, preferably from 60 seconds to about 5 minutes. The period of time can be optimised for any particular method being performed. It should also be noted that there will be a delay after administration of the oxygen carrier before the oxygen carrier arrives at the target region. Thus there will be a delay before changes in deoxyhaemoglobin levels are observed in the target region. This delay will depend, inter alia, on the route and site of administration, and on the particular animal being examined.

Conveniently measurements can be taken throughout the entire course of the method. Alternatively, it may be desirable to take measurements only during specific periods of time, e.g. when a baseline is being determined and when changes in signal are expected to be observed in the target region. In either case a series of images can be taken at suitable time intervals over the relevant period(s) of time. For example, an image could be taken every second (or more or less frequently as desired) over the course of the relevant period of time.

It is preferred that the baseline measurement is taken before the administration of the oxygen carrier. However, it is possible that the baseline measurement is taken after administration of the oxygen carrier, but before the oxygen carrier has reached the target region. In another possibility, the baseline measurement could be obtained retrospectively after the effects of the oxygen carrier have substantially ceased. Typically taking the baseline before the oxygen carrier is administered is preferred because it is simpler and reduces the possibility of errors occurring.

Without wishing to be bound by theory, it is believed that the cells in the penumbra are still alive and that they maintain the ability to perform their physiological function. However, the cells are hypoxic and thus no significant activity occurs. For example, in the case of neurons, the cells in the penumbra remain viable but do not perform conventional neurological activities. When the cells within the penumbra are oxygenated by the extra oxygen supplied by the oxygen carrier, the cells are able to become more active. Without addition of the oxygen carrier the cells remain in a largely quiescent state. In the case of neurons this activation by the oxygen carrier seemingly results in a wave of depolarisation across the penumbra. This activity results in the consumption of oxygen to provide the requisite energy in the cells (i.e. in the form of ATP), and therefore results in the conversion of oxyhaemoglobin to deoxyhaemoglobin. The increase in deoxyhaemoglobin caused a reduction in a $T_2^*$ MRI signal.

The method may optionally involve observing for a temporal-spatial wave of signal change in at least a part of the target region following administration of the oxygen carrier. In particular the method may involve observing for a change in signal indicative of higher levels of deoxyhaemoglobin moving from an ischaemic core outwards, i.e. towards surrounding, non-ischaemic tissues. Such a wave has been observed to be a particular characteristic of an ischaemic penumbra.

It is a particular advantage of the present invention that the penumbra can be clearly visualised and differentiated from both the surrounding non-ischaemic tissues and the ischaemic core.

Preferably in step i) the oxygen is administered orally, e.g. by inhalation. Preferably the oxygen is administered at a fraction of inspired oxygen ($FiO_2$) above atmospheric oxygen concentrations. Preferably the fraction of inspired oxygen is from 25% to 100%, more preferably from 30% to 100%. Desirably the $FiO_2$ is sufficient to result in substantially complete oxygenation of the animals blood supply, but which does not cause harm to the animal. Suitable levels of oxygen for administration to any particular animal can be readily determined by the skilled person.

Preferably oxygen is administered to the animal throughout at least steps i) to iv) of the method such that the animal is hyperoxic throughout all the measuring steps. It is desirable that the baseline and second measurements are both made when the animal is hyperoxic in order that useful and consistent data is obtained. Suitably the oxygen is administered to the patient continuously throughout the entire method, and optionally also before and afterwards. Preferably the oxygen administered to the patient is kept at a substantially constant level (e.g. $FiO_2$ for inhaled oxygen) at least during the period of time the measurements are taken, and preferably throughout the entire duration of the method.

By "hyperoxic" is meant above normal occurring levels of oxygen in the relevant context. For example a hyperoxic animal contains levels of oxygen which are above those that would result from normal respiration of atmospheric air. A hyperoxic source of gas for inhalation contains more oxygen that is present in atmospheric air. A hyperoxic animal will be the result of it inhaling hyperoxic air.

It is an important feature of the present invention that the animal is hyperoxic, because this increased inspired oxygen within the lungs and circulation is picked up and delivered by the oxygen carrier to the penumbra and it is this which stimulates the activation leading to the observed MRI signal change enabling detection of the penumbra. The induction of hyperoxia is key to creating the additional oxygen which can be taken up and delivered to the target tissue by the oxygen carrier more efficiently than plasma.

In a highly preferred embodiment the method is used to identify the penumbra associated with an ischaemic event in the central nervous system, e.g. the brain, of an animal. For example, in a particularly preferred embodiment the method is used to identify the extent of the penumbra (e.g. a cortical penumbra) following a stroke.

The animal which is the subject of the method of the present invention may be essentially any animal. However, in preferred embodiments the animal is a vertebrate, more preferably a mammal, and most preferably a human.

The term "oxygen carrier" means a material, preferably a liquid, which is able to releasably take up and release oxygen. In particular, the oxygen carrier should be able to take up and release oxygen more readily than plasma. For example, the oxygen carrier may be a liquid which is able to dissolve oxygen at relatively high quantities (e.g. 5% v/v or more, preferably 10% v/v or higher, more preferably 20% v/v or higher). Preferably the oxygen carrier is biocompatible, and more preferably it is a physiologically inert oxygen carrier. Suitable oxygen carriers include perfluorocarbons (PFCs), which are probably the best known liquid oxygen carriers and which are currently used in various types of surgery. Exemplary PFCs for use in the present invention include FC-75 (a fluorocarbon derivative of tetrahydrofuran with the chemical formula $C_8F_{16}O$), perflubron (perfluorooctyl bromide), and perfluorodecalin (a fluorocarbon derivative of decalin with the formula $C_{10}F_{18}$). 100 ml perfluorodecalin, for example, can dissolve 49 ml of oxygen at standard pressure and temperature, which is many fold higher than plasma.

In some preferred embodiments the oxygen carrier may be an emulsion of small particles in a suitable medium (e.g. water or saline). For example, the particles of the emulsion can have a median diameter of 0.2 µm or less. Methods of forming such emulsions will be apparent to the skilled person.

The oxygen carrier is preferably delivered as a bolus having a sharply defined start, and preferably also a sharply defined end. By sharply defined it is meant that the administration profile does not taper gradually upwards, but rather it is initiated at a relatively high rate. Preferably the administration is also terminated sharply without a gradual taper off. Providing the oxygen carrier in such a manner is advantageous as it allows a clear resolution the effects of the oxygen carrier in the target region when it arrives. If the oxygen carrier were administered gradually, i.e. at a low rate over a protracted period, then it would be more difficult to clearly identify changes in metabolic activities in the region of interest as a result of the oxygen carrier. In particular, the wave of neuronal activity, which is a desirable observation of the present invention, would be most clearly visible where an abrupt change in oxygen levels occurs in the region of interest. The administration profile of the oxygen carrier can of course be optimised for the particular animal being examined and also for the particular assessment paradigm.

Typically the total quantity of oxygen carrier administered will be in the range of 1 to 3 ml per kg body weight. However, it will be understood that he amount of oxygen carrier administered can be optimised to the particular method and to the particular animal, and the amount will vary depending on the particular properties of the oxygen carrier. Such optimisation is a routine matter for the skilled person.

The method may further comprise taking a decision based on the measurements which affects the therapeutic treatment of the animal, e.g. by surgery or medication. The decision about the appropriate treatment of the animal will depend on the results of the comparison of step v). For example, the method may include deciding whether to administer thrombolytic treatment to the animal in the case of an infarction. In one particularly preferred embodiment the method provides useful information to allow a clinician to decide on the best course of treatment following a stroke (including TIA). Where the method of the present invention reveals there is little or no penumbra surrounding the ischaemic core then thrombolysis may be undesirable. Where, on the other hand, there is a clear penumbra, particularly an extensive one, thrombolysis may be desirable. Steps i) to iv) of the present method allow such a decision to be made based on the true status of the tissues of the animal rather than indirect inferences.

The 'target region' is typically the region surrounding or containing an ischaemic core, e.g. the region of the brain which contains a site of infarct in a stroke. However, the target region could be any region of interest. The target region can be 2- or 3-dimensional, i.e. it can be an area or a volume. MRI is well adapted to observing a 3 dimensional region. Typically the target region will be a 3-dimensional volume, but in some situations it may be perfectly satisfactory to simply observe a 2-dimensional area.

It is a preferable feature of the present invention that the animal is hyperoxic over the entire course of the method. Where an animal is experiencing an ischaemic event, e.g. a stroke, trans-ischaemic event (TIA) or a heart attack, then it is often clinically desirable to administer oxygen to the animal to alleviate symptoms and reduce harm. It is therefore undesirable that the supply of oxygen be disrupted to perform a procedure such as MRI. The present invention is compatible with the continuous administration of oxygen in such a setting.

In a further aspect the present invention comprises a diagnostic method comprising the steps set out above and the further step of deciding, based upon the comparison of step v), on the appropriate course of treatment for the animal.

In a further aspect there is provided an MRI scanner system specifically adapted to perform the methods described above. Said system may comprise an MRI scanner, apparatus adapted to provide oxygen to the patient via inhalation, and apparatus suitable to administer the oxygen carrier. The system may further comprise a source of oxygen gas and a source of the oxygen carrier.

In a further aspect the present invention provides the use of an oxygen carrier, e.g. a PFC, in a method of imaging the metabolic function in a target region of an animal using magnetic resonance imaging as set out above.

Embodiments of the present invention will now be described, by way of example only, with reference to the accompanying drawings, in which.

EXAMPLE 1—IN VIVO ASSESSMENT OF IMPROVED MRI PARADIGM IN RATS

Following middle cerebral artery occlusion (MCAO) in rats, we have shown a sudden reduction of a MRI $T_2^*$ signal following the injection of perfluorocarbon (PFC) with hyperoxia.

The following protocol was used to develop this technique whereby penumbra is identified by a negative $T_2^*$ response in an anaesthetised rat following induction of stroke:

The animal was transferred to the magnet bore and stroke was confirmed using diffusion and perfusion weighted imaging. Hyperoxia was induced by increasing $FiO_2$ (fraction of inspired oxygen, 100% in FIG. 1). Following a period of stabilization the $T_2^*$ scan was started with the animal on hyperoxic ventilation and the PFC was injected i.v. as a bolus (3 ml/kg in FIG. 1). The region of negative $T_2^*$ was identified by creating a map modeling the change in response between baseline (on hyperoxia) and the negative dip illustrated in FIG. 1D. The optimal combination of $FiO_2$ (typically in the range 30%-100%, preferably 40%-100%) and PFC dose (typically in the range 1 ml-3 ml/kg) will be determined by ongoing studies.

Figure 1:
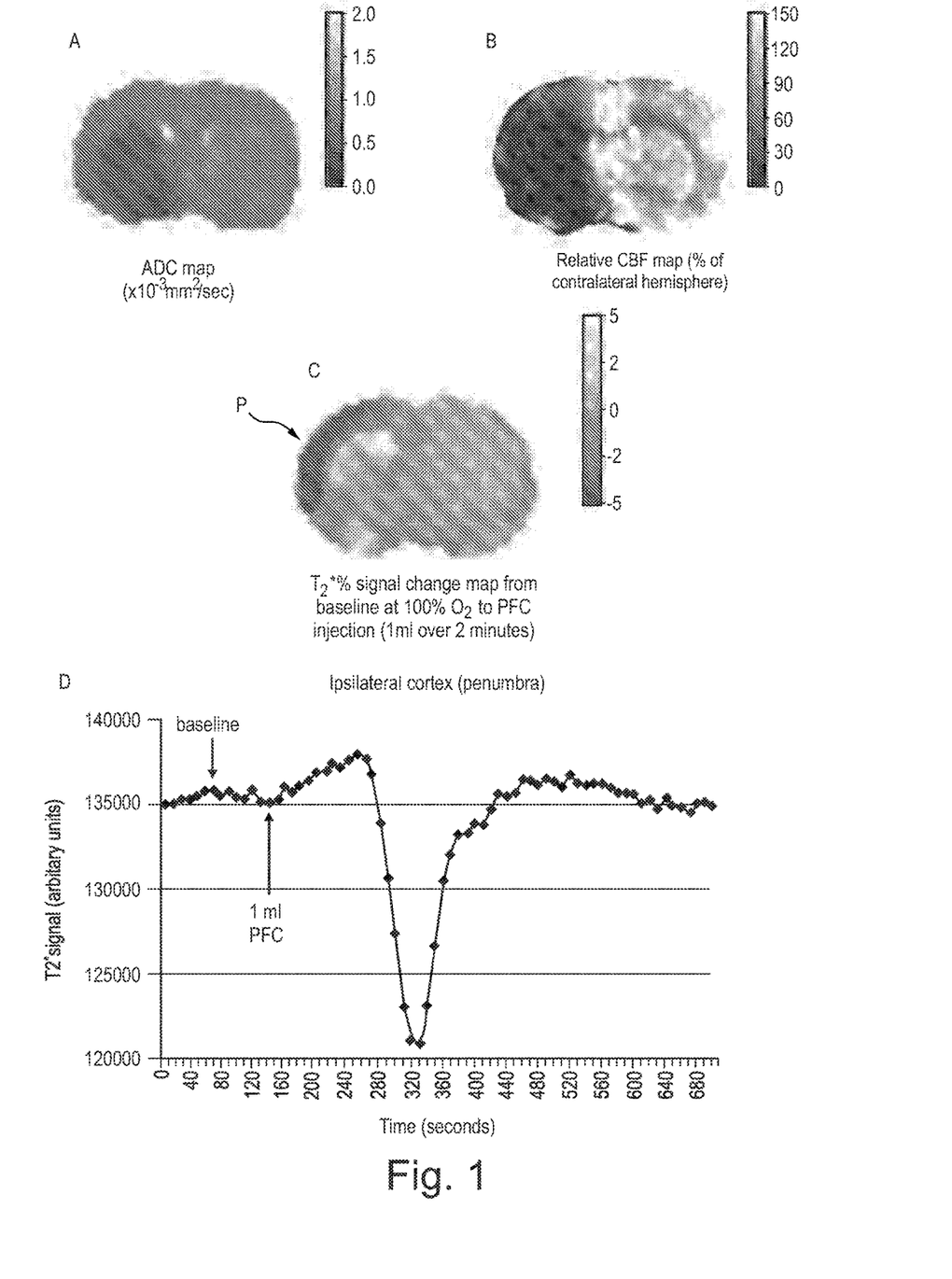
FIG. 1 shows (A) Apparent diffusion coefficient map showing region of acute ischaemic damage (B) Relative cerebral blood flow map showing region of hypoperfusion (C) $T_2^*$ percentage change map generated by comparing signal during baseline (animal breathing 100% oxygen) to signal during PFC injection (on 100% oxygen). The dark area of decreased signal was specific to the region of interest (ROI) designated as ipsilateral cortex (P: presumed penumbra) (D) The time course of the $T_2^*$ response in the ipsilateral cortex ROI. Approximately 2 minutes of baseline $T_2^*$ was acquired with the animal breathing 100% oxygen, following which 1 ml of PFC was injected intravenously over a period of 2 minutes.

This negative $T_2^*$ response was specific to a region of the brain where blood flow was reduced but ischaemia was not indicative of irreversible acute damage (FIGS. 1A & B). This region is the penumbra.

Figure 2:
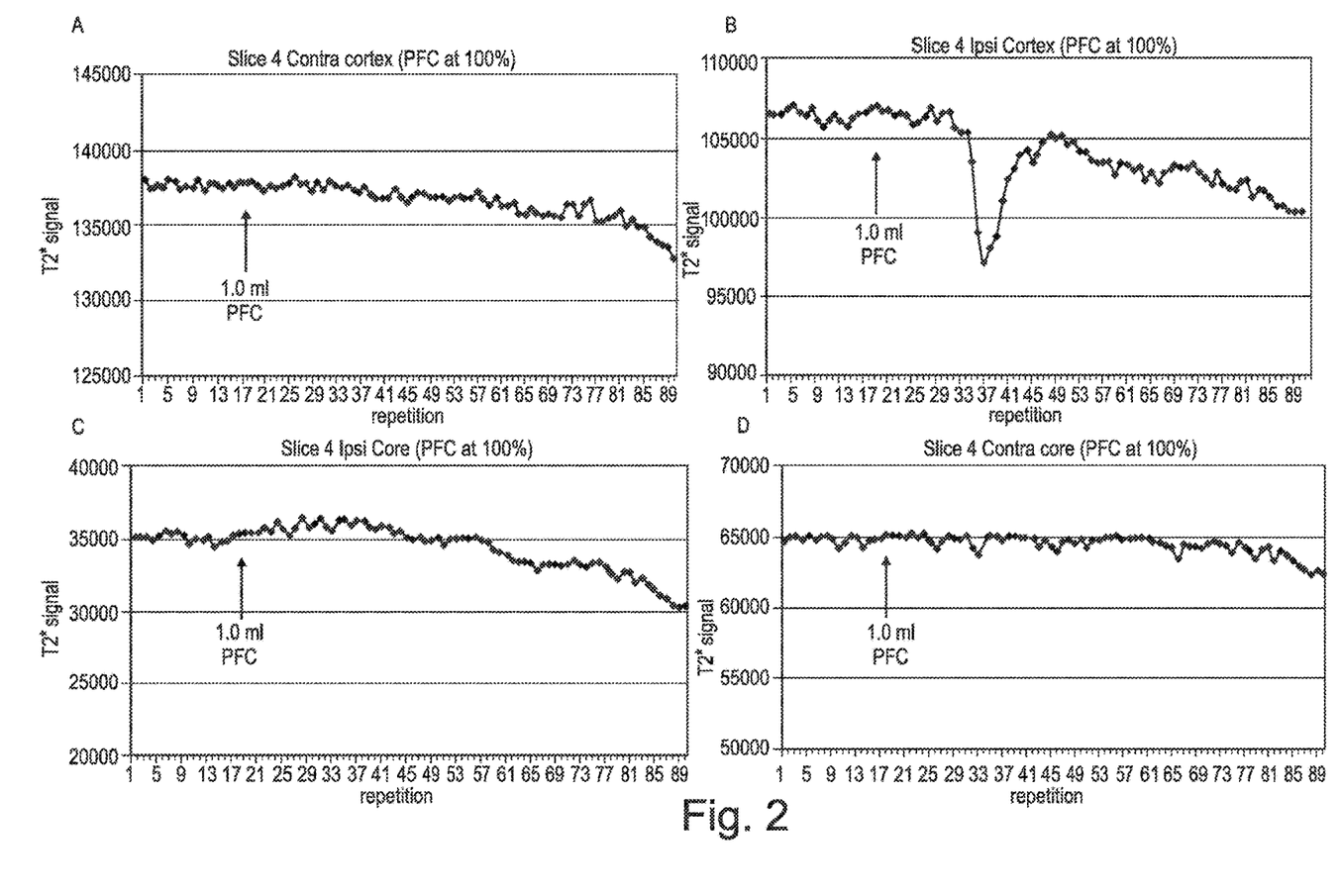
FIG. 2 shows the time course of the $T_2^*$ response in (A) the normal contralateral cortex (B) ipsilateral cortex (penumbra) (C) ischaemic core and (D) corresponding contralateral region. Baseline $T_2^*$ was acquired with the animal breathing 100% oxygen, following which 1 ml of PFC was injected intravenously over a period of 2 minutes.

This T2* signal reduction does not take place in other regions of the brain such as the ischaemic core or the normal contralateral tissues as shown in FIG. 2.

Figure 3:
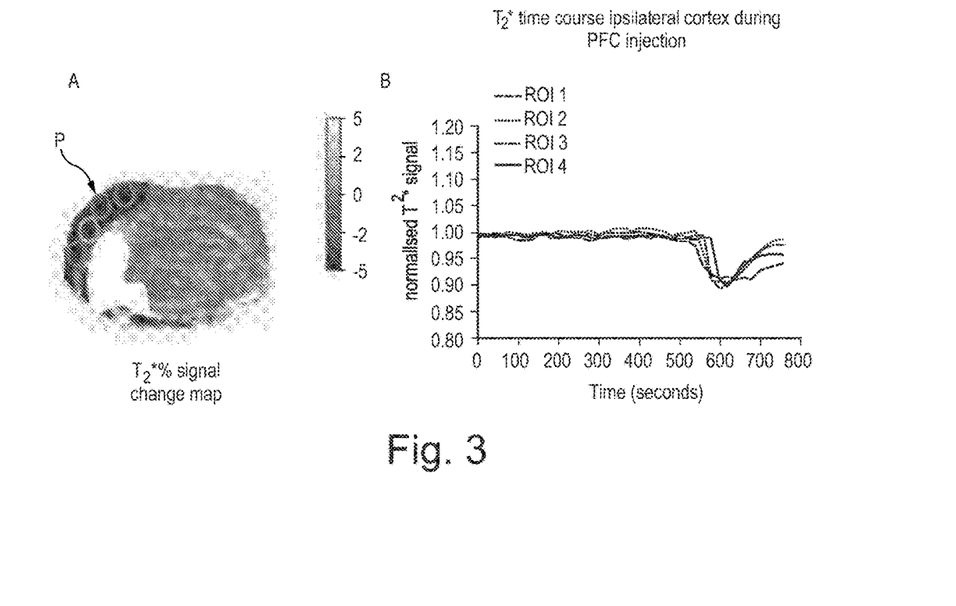
FIG. 3 shows (A) $T_2^*$ percentage change map generated by comparing signal during baseline (animal breathing 40% oxygen) to signal at end of PFC injection (on 40% oxygen). The dark area of decreased signal was specific to the region of interest designated as ipsilateral cortex (P: presumed penumbra). White region indicates ischaemic core. Coloured circles represent regions of interest used for time course shown in graph (B) time course of the $T_2^*$ response in the ipsilateral cortex regions of interest. It is evident that the decrease in $T_2^*$ signal occurs later in regions of interest furthest from ischaemic core.

This reduction in T2* signal travels from the ischaemic border zone region in a direction starting from the tissues closest to the core and thus has temporo-spatial dimensions as shown in FIG. 3.

Figure 4:
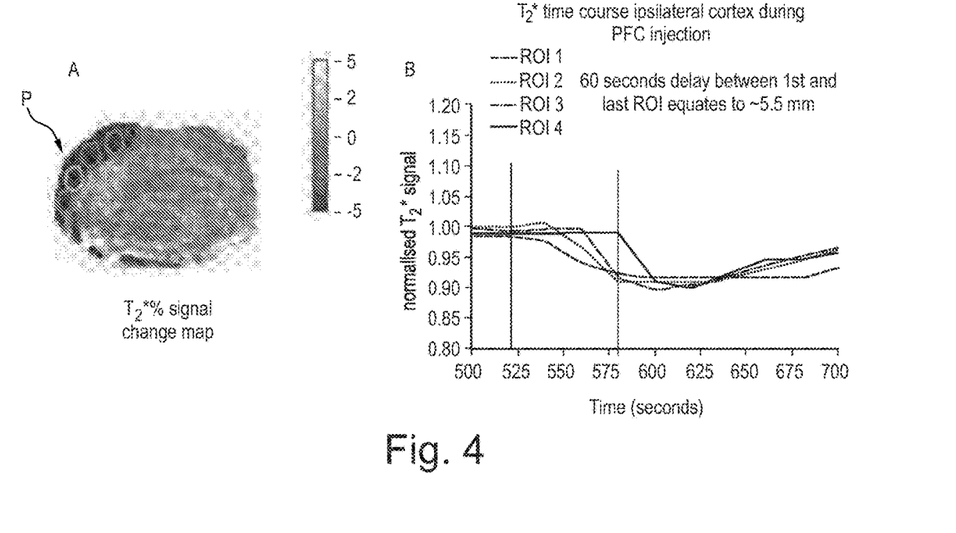
FIG. 4 shows (A) $T_2^*$ percentage change map generated by comparing signal during baseline (animal breathing 40% oxygen) to signal at end of PFC injection (on 40% oxygen). The dark area of decreased signal was specific to the region of interest designated as ipsilateral cortex (P: presumed penumbra). Coloured circles represent regions of interest used for time course shown in graph (B) time course of the $T_2^*$ response in the ipsilateral cortex regions of interest showing temporo-spatial nature of the response.

Spreading depression is an electrical wave of depolarisation that propagates through neural tissue at 2-5 mm/min and was first described in literature in 1944 (Leao, 1944). Branston et al showed spreading depolarisations in the periphery of ischemic regions in the baboon (Branston et al, 1977). Others have subsequently shown it in other animals and also humans (Fabricus et al, 2006). The speed of T2* signal wave following injection of PFC is approximately 5 mm/min as shown in FIGS. 4a and b, which is the similar to the speed of the spreading depolarisation wave.

Following the depolarisation near infrared spectroscopy has shown an increase of deoxyhaemoglobin (Wolf et al, 1997) which causes the reduction in T2* signal. This increase in deoxyhaemoglobin is due to the utilisation of oxygen to produce the energy, i.e. ATP, required by the $Na^+/K^+$ pumps to repolarise the membrane. Depolarisations can only occur if metabolic processes and the neuronal membranes are intact. The definition of the ischaemic penumbra by Astrup and colleagues was based on electrical activity and metabolism, i.e. tissues with reduced blood flow with an upper threshold of electrical failure and lower threshold of energy failure. Therefore we have identified the penumbra based on metabolic change following electrical activity stimulated by intravenous perfluorocarbon infusion with hyperoxia.

EXAMPLE 2—GENERAL METHODOLOGY

The methods described in this application provide a scanning paradigm which allows qualitative or semi-quantitative measures of metabolism in a target tissue (e.g. the brain). This paradigm involves administration of an oxygen carrier (e.g. a PFC) to a hyperoxic animal during an MRI scanning procedure. By analysing the variation of the signal indicating deoxyhaemoglobin levels following oxygen carrier administration it is possible to produce semi-quantitative metabolic maps. The methods are especially useful in identifying the ischaemic penumbra following a stroke or other infarction.

In the present invention the subject is caused to inhale oxygen. The oxygen may be administered via a face mask. This technique is easy and generally acceptable to patients.

Oxygen Carriers

There are a variety of known blood replacement products or blood expanders which include oxygen carriers offering the capability of delivering oxygen for release to tissues. It is envisaged that any such suitable oxygen carrier, which may be administered intravenously could be considered for the purpose of providing a bolus of oxygen to the target region. One particular type of oxygen carrier considered to be suitable for this purpose would be perfluorocarbons (also known as perfluorochemicals). Because this is the most common and well-known family of oxygen carrier the following discussion will focus upon them. However, it should be understood that other chemicals could be used provided they are not harmful to the animal (i.e. are biocompatible) and have the desired oxygen carrying properties.

Perfluorocarbons are chemically inert synthetic molecules that consist primarily of carbon and fluorine atoms, and are clear, colourless liquids. They have the ability to physically dissolve significant quantities of many gases including oxygen and carbon dioxide. Perfluorocarbons are hydrophobic, and are therefore not miscible with water.

Perfluorocarbons thus typically have to be emulsified for intravenous use. With sophisticated technology, it is possible to generate a stable perfluorocarbon emulsion with exceptionally small particles (median diameter <0.2 μm). Oxygen transport characteristics of perfluorocarbon emulsions are fundamentally different from those of blood. Perfluorocarbon emulsions are characterized by a linear relationship between oxygen partial pressure and oxygen content, in contrast to blood which exhibits a sigmoid oxygen dissociation curve.

Therefore the oxygen carrying capacity is directly proportional to $pO_2$ and this means that the amount of oxygen carried by perfluorocarbons can be varied by varying the $pO_2$. The oxygen transport characteristics and ability to vary the oxygen carrying capacity, makes perfluorocarbons ideal to use as an agent to carry oxygen in the present method. As the oxygen carrying capacity can be varied stratification of the tissues based on their metabolic rates can be obtained. The intravenous route has been routinely used in clinical practice. The first perfluorocarbon used as a compound to carry and deliver oxygen was Fluosol™ approved in 1989 by FDA. However this product manufactured by Green Cross needed to be frozen for storage and thawed before use. An alternative product Oxygent™ is not frozen but is in a ready to use form.

It is expected that any suitable perfluorocarbon or physiologically inert oxygen carrier commercially available, or others that may yet be made available could be used for the purpose of oxygen delivery in the present method.

The $pO_2$ of air at normal atmospheric pressure is 160 mm of Hg and the percentage of oxygen is 21%. This means that as the perfluorocarbon passes through the lungs, the oxygen would bind to it and the amount of oxygen within the bolus of perfluorocarbon could be up to 21% (depending on the degree of mixing of blood and agent which takes place). Since the binding of oxygen to perfluorocarbons is 1:1, if the inhaled oxygen is increased to, say, 30% the oxygen carrying of the perfluorocarbon could be up to 30% and further increases in oxygen concentration would result in a corresponding increase in perfluorocarbon oxygen content. Thus intravenous administration of perfluorocarbon can result in an $O_2$ concentration of 21% or higher, compared to standard blood oxygen concentrations which achieve about 3-4%.

General Methodology

The method is carried out via intravenous injection of an oxygen carrier whilst the patient breathes an oxygen rich gas, e.g. air enriched for oxygen or even pure oxygen.

A suitable general method for performing magnetic resonance imaging scan illustrative of the invention comprises:

Patient is positioned in an MRI scanner.

Patient is provided with a hyperoxc gas mixture, typically via a face mask.

Scanning starts. The scanning sequence collects whole or partial brain scans (or any other part of the body under investigation) repeatedly over the course of the study resulting in a number of volumes providing temporal information. This scan runs continuously until step 6 is completed.

Scan proceeds and data is recorded for a specified time with hyperoxic oxygen inhalation. This provides baseline data for future image analysis and comparison.

A specified amount of an oxygen carrier is injected, preferably delivered rapidly over short period of time.

The scan continues and the target region is observed for changes in signal. Data is collected continuously for a suitable period of time, typically 5 to 10 minutes. The signal changes occur as a result of changes in the levels of deoxyhaemoglobin.

The data from this scan is then analysed using image analysis software to provide quantitative or qualitative measures of the oxidative metabolic activity within the tissues being scanned.

A change in metabolic activity in a target region or part of a target region will be indicative of the status of the tissues. In penumbra tissues there will be a characteristic alteration in signal as the cells become active when they become oxygenated by the oxygen provided by the oxygen carrier. This will result in an increase in deoxyhaemoglobin, and this may be observed as a consequential decrease in $T_2^*$ signal. The change in signal has been observed to take the form of a wave which moves across the penumbra, beginning at the core of infarct and moving towards the boundary of the penumbra and surrounding, unaffected tissue.

As discussed briefly above, the optimum amount of oxygen carrier to be injected can be determined by the skilled person for the particular animal and the particular paradigm being used. The oxygen carrier is preferably administered as a bolus, i.e. essentially as one substantially instantaneous dose and not over a protracted period of time. Administration as a bolus in this manner allows for improved resolution of changes occurring in the target region. The signal changes occur sharply once the oxygen carrier arrives at the target region. If the oxygen carrier were administered gradually then any changes in the target are of interest would not be as clearly defined because changes would happen gradually. Furthermore, the characteristic and informative wave of activity which is observed to pass across the penumbra would not be so clearly discernable if the oxygen carrier were not administered as a sharp bolus.

In addition to being useful for modelling the metabolic function of tissues, the described method can be used to assess the metabolic function of normal and diseased tissues and organs. These can be compared to assist in the diagnosis of disease states and analysis of tissue and organ states. Due to the general applicability of the method the types of disease which can be investigated and diagnosed are not limited, but for illustrative purposes may include ischaemic incidents such as stroke; epilepsy; dementia, including Alzheimer's disease; multiple sclerosis; cancer and cardiac disease.

Stroke

Stroke is the third most common cause of death and the largest single cause of severe disability. The cost for society is also very high and the average cost per patient across Europe is about 15,000 Euro per patient during the first year. The therapeutic strategies to treat stroke aim to limit cerebral ischaemia by early reperfusion and interference with the patho-biochemical cascade leading to ischaemic cell death (Heiss et al). Therapy can only be effective if there is viable and potentially salvageable brain tissue. The term "ischaemic penumbra" is used to define this viable brain tissue (Baron, Benard Schaller). Ideally one would want to stratify the injured tissue along haemodynamic, functional and metabolic dimensions (Hakim A M). The potential time window for the various treatment options is variable, since the penumbra may last up to 48 hours in some patients (Heiss W D and Marchal M E). The time window for, starting reperfusion-based treatments is very short (thrombolytic measures), longer for neuroprotection and longer still for antioxidant and anti-apoptotic measures. For all these treatment options it is first necessary to establish the presence and extent of the penumbra. Imaging is the only direct way of assessing the penumbra. Positron Emission Tomography (PET) imaging is considered the reference standard for the evaluation of the pathophysiological changes in early stroke (Baron J C). However, its use in clinical practice is not practical, as it is complex, costly and not readily available.

The technique of the present invention should prove easy to translate into this clinical situation.

Epilepsy

Epilepsy or recurrent seizure is a common disorder with a prevalence of approximately 1:130 in the UK. Most adult epilepsies are focal. About 30% are not brought under satisfactory control using drug treatment and increasingly surgical treatment is being considered. In these cases it is very important to identify the seizure focus for surgery. Patients are investigated prior to surgery with EEG, structural MRI, SPECT and PET. EEG is used to pick up the abnormal electrical activity generated by the seizure focus. However, surface EEG studies cannot accurately localise the abnormality within the brain. Nevertheless this can be done by placing electrodes into the brain, although this carries risks due to the invasive nature of the technique. Studies have shown altered metabolism within the seizure focus. During the ictus there is increased metabolism and blood flow and this reduces post-ictally. Therefore, techniques with the ability to anatomically demonstrate altered blood flow such as SPECT and altered metabolism such as PET 18FDG are also used to demonstrate the seizure focus. However the main drawbacks, common to both these techniques are the use of radio-isotopes and relatively limited spatial resolution. In addition the cost of PET scans is very high. Using the above described method the inventors believe it would be able to non-invasively demonstrate the seizure focus. The advantages of MRI are that it does not use ionising radiation, has higher spatial resolution, it is ubiquitous and has a lower cost than PET.

Dementia

Dementia, a progressive brain dysfunction, leads to a gradually increasing restriction of daily activities. Dementia not only affects patients, but also those surrounding them, as most patients require care in the long-term. The most well-known type of dementia is Alzheimer's disease. The Alzheimer's Society estimates that there are currently over 750,000 people in the UK with dementia.

Current theories on the pathogenesis of the cognitive signs and symptoms of Alzheimer's disease attribute some of them to a deficiency of cholinergic neurotransmission. Donepezil hydrochloride a drug used in Alzheimer's disease is postulated to exert its therapeutic effect by enhancing cholinergic function and improve cognitive performance in patients for unto a year. This drug treatment is expensive and there are many other causes of dementia, for which this treatment is not effective.

Therefore, diagnosis of this condition is important and this is currently achieved using SPECT or PET scans, which show reduced blood flow and metabolism in the temporal and parietal lobes of the brain.

It is postulated that this specific pattern could also be detected by the methods of the present invention.

Multiple Sclerosis

MS is thought to be an autoimmune disease that affects the central nervous system (CNS). The CNS consists of the brain, spinal cord, and the optic nerves. Surrounding and protecting the nerve fibers of the CNS is a fatty tissue called myelin, which helps nerve fibers conduct electrical impulses. Myelin not only protects nerve fibers, but makes conduction possible. When myelin or the nerve fibre is destroyed or damaged, the ability of the nerves to conduct electrical impulses to and from the brain is disrupted, and this produces the various symptoms of MS. MRI scans are the most sensitive way of detecting the lesions in MS. However plain MRI scans cannot differentiate actively inflamed lesions from older healed lesions. Gadolinium enhanced scans can demonstrate actively inflamed lesions as the blood brain barrier is disrupted. Since the metabolism of an active lesion would be different from the older healed lesions, it is postulated that methods of the present invention could demonstrate the actively inflamed lesions on this basis.

Cancer

Over 270,000 new patients are diagnosed with cancer annually in the UK. Cross-sectional imaging using MRI and CT, currently have a central role for the management of patients with malignant disease. This role includes initial diagnosis and staging, monitoring response to treatment and recognition of complications. The use of size as a criterion of lymph nodal involvement has its limitations. Tumour tissues have a higher level of metabolism and this has been used to detect cancer dissemination within lymph nodes, by combing structural CT scans with PET 18FDG. It is believed that the above described technique will demonstrate tissues that are metabolically different, and with high resolution structural MRI scans, can replace PET-CT staging cancer. This will have an impact not only on costs but also the ability to deliver results quickly, as MRI scanners are ubiquitous and the technique will be easy to translate clinically. As MRI imaging does not use ionising radiation, the response of treatment can be more closely monitored, since there no limitations on the number of times the patient or the time intervals before imaging can be repeated. Therefore the present method could be used in staging head and neck cancers, lung cancers, gastrointestinal cancers, genitourinary cancers, lymphoma and melanoma. This ability to monitor development or progression of cancer from a primary tumour to metastases by targeting particular tissue (e.g. lymph nodes) or organs (e.g. liver) is a significant development in the care of cancer sufferers. The method can also be used in differentiating tumour recurrence from tumour necrosis in brain gliomas.

Cardiac Imaging

In the U.K. 140,000 people die every year from heart disease. Narrowing of the coronary arteries can result in insufficient blood supply to the heart, especially at times of physical or emotional stress. The narrowing of the arteries is due to deposition of cholesterol plaques on the inner wall of the artery. The lack of oxygenated blood due to coronary artery disease causes the heart muscle to go into anaerobic metabolism, producing a cramp-like pain known as angina. The lack of oxygen for more than a short period causes ischaemia and/or muscle cell death. Computed tomography coronary angiography (CTCA) is a technique for non-invasive detection of the narrowing of a blood vessel (coronary stenosis). CTCA is an excellent tool to rule out relevant coronary artery disease, but not every plaque or lesion of the coronary arteries causes significant reduction of blood flow to the heart.

Myocardial perfusion (blood flow) imaging using single photon emission computed tomography (SPECT) is an established method for assessing the physiologic significance of coronary lesions in patients with chest pain. Combining these two imaging modalities of the heart has provided both anatomical and physiological information for better management of cardiac ischaemia. Now cardiac MRI can also provide an accurate picture of the heart. It can capture the heart beating in real time by imaging up to 50 frames per second in a sequence triggered by an electrocardiogram (EKG) machine. These capabilities allow us to see the coronary arteries in enough detail to determine whether plaque accumulation or blockages have occurred. Cardiac MRI can also determine the extent of muscle damage following a heart attack, because MRI has good soft tissue contrast and so can identify the subtle differences between normal and abnormal heart muscles. However this is still information is still only structural. Ideally one would require information that would be, able to stratify affected tissues on the basis of function. Cardiac tissues that are functionally active will have higher metabolism and therefore imaging of the heart using the current method can stratify tissues that are normal, ischaemic and infracted.

Advantageously the method of the present invention is envisaged to have application in the management of many common diseases. A benefit of the procedures described herein lies in the fact that the data relating to metabolic function (or dysfunction) of tissue is available in real time, yielding valuable information about viable tissue, and enabling a quick decision to be taken if an intervention or procedure has to be considered as a consequence of a diagnosis made on the base of the data gathered.

Discussion

The technique of the present invention is different from, and provides advantages compared to, the oxygen challenge methods described in WO2008/023176. In particular:

In the technique of the present invention the penumbra is identified by the reduction in signal due to an increase in deoxyhaemoglobin which returns back to the base line, whereas in the methods of WO2008/023176 the penumbra is identified by an increase in signal due to a reduction in the deoxyhaemoglobin followed by a decrease in signal. The signal changes are the opposite of each other as the mechanisms are different.

Signal change occurs only in penumbra in the techniques of the present invention, but the in WO2008/023176 signal change take place in the penumbra and normal tissues but the intensities are different and this helps separate them. The present invention thus provides an improvement in differentiating the penumbra from surrounding tissues.

The technique of the present invention is able to identify the penumbra from the temporal and directional information present in the data, where as in the methods of WO2008/023176 it is only the differences in signal intensity that helps identify the penumbra. This again allows for better resolution in the techniques of the present invention.

In the technique of the present invention the penumbra is identified due to metabolic changes brought about by an electrical discharge stimulated by an intravenous injection of an oxygen carrier (e.g. a perflurocarbon) with the animal breathing hyperoxia. In the method of WO2008/023176 the timing of the injection is not critical.

The present invention is particularly relevant in a clinical context where an animal may well be receiving additional oxygen to manage their clinical condition. This administration of oxygen will not interfere with the technique and thus there is no need to stop or modify this ongoing treatment.

The present invention allows a rapid test to be performed in a limited number of steps, and does not require that oxygen administration be altered several times over a protracted period.

Various preferred embodiments of the present invention have been described above. However, it should be understood that the invention is not restricted to the preferred embodiments and various modification to the methods can be made to the methods of the present invention without departing from the scope and spirit of the invention.

REFERENCES

Astrup J, Siesjo B K and Symon L, Thresholds in cerebral ischemia—the ischemic penumbra. Stroke. 12:723-725. 1981.
Fenstemacher M J and Narayana P. Serial proton magnetic resonance spectroscopy of ischemic brain injury in humans. Investigative Radiology. 25(9):1034-9, 1990.
Houkin K. Proton and phosphorous-31 nuclear magnetic resonance spectroscopy in experimental cerebral infarction in rats. Hokkaido Igaku Zasshi (Japanese). 65(6): 595-603.
Law R, Bukwirwa H (1999) The Physiology of Oxygen Delivery.
Pauling L, Coryell C, The magnetic properties of and structure of haemoglobin, oxyhaemoglobin and carbonmonoxyhaemoglobin. Proc Natl Acad Sci USA 22:210-216.
Ogawa S, Lee T M, Kay A R, Tank D W. Brain magnetic resonance imaging with contrast dependent on blood oxygenation. Proc Natl Acad Sci USA. 1990: 87; 9868-9872. 3. Heiss W D, Thiel A, Grand M, Graf R (1999), Which targets are relevant for therapy of acute ischaemic stroke? Stroke 30:1486-1489.
Baron J, Mapping the ischaemic penumbra with PET: implications for stroke treatment. Cerebrovasc Dis. 1999; 9:193-201.
Benard Schaller, Review article. Cerebral Ischaemia and Reperfusion: The Pathophysiologic Concept as a Basis for Clinical Therapy. Journal of Cerebral Blood Flow & Metabolism. 24:351-371 2004.
Hakim A M, The cerebral ischemic penumbra. Can J Neurol Sci. 1987; 14:557-559.
Heiss W D, Huber M, Fink G R, et al., Progressive derangement of peri-infarct viable tissue in ischemic stroke. J Cereb Blood Flow Metab. 1992; 12:193-203.
Marchal G, Beaudouin V, Rioux P, et al., Prolonged persistence of substantial volumes of potentially viable brain tissue after stroke: a correlative PET-CT study with voxel-based data analysis. Stroke. 1996; 27:599-606.
Guadagno J V, et al., Cerebrovascular Diseases 19(4), 239-246, Feb. 2005. 10.
Keipert P E: Perfluorochennical emulsions: future alternatives to transfusion. Blood Subst Princ Meth Prod Clin Trials 1998, 2:127-156.
Leao A A P. Spreading depression of activity in cerebral cortex. *J Neurophysiol* (1944) 7:359-90.
Branston N M, Strong A J, Symon L. Extracellular potassium activity, evoked potential and tissue blood flow. Relationships during progressive ischemia in baboon cerebral cortex. *J. Neurol. Sci.* (1977) 32:305-321.
Fabricius M, Fuhr S, Bhatia R, Boutelle M, Hashemi P, Strong A and Lauritzen M. Cortical spreading depression and peri-infarct depolarization in acutely injured human cerebral cortex. *Brain* (2006) 129:778-790.
Wolf T, Lindauer U, Reuter U, Back T, Villringer A, Einhaupl K and Dirnagl. Noninvasive Near Infrared Spectroscopy Monitering of Regional Cerebral Blood. Oxygenation Changes During Peri-Infarct Depolarizations in Focal Cerebral lschemia in the Rat. Journal of Cerebral Blood Flow and Metabolism (1997) 17:950-954.

The invention claimed is:

1. A method of imaging metabolic function in a target region of an animal using magnetic resonance imaging, the method comprising the steps of:
   i) administering oxygen to said animal such that the animal is hyperoxic;
   ii) obtaining a baseline measurement of a signal indicative of deoxyhaemoglobin level in a target region of the hyperoxic animal;
   iii) administering an oxygen carrier to the hyperoxic animal such that it will enter the blood supply of the animal;
   iv) obtaining at least one second measurement of a signal indicative of deoxyhaemoglobin level in the target region of the hyperoxic animal following administration of the oxygen carrier; and,
   v) comparing said baseline and second measurements to obtain data relating to the relative amounts of deoxyhaemoglobin present in said target region in the baseline measurement and following administration of the oxygen carrier, and correlating said data to the metabolic function of the target region.

2. The method of claim 1, wherein the target region is in the brain of said animal.

3. The method of claim 1, comprising observing in step v) a change in the signal in the target region which is indicative of an increase in deoxyhaemoglobin levels, which increase is indicative of a penumbra.

4. The method of claim 1, comprising identifying a penumbra in a region of the brain of said animal.

5. The method of claim 1, comprising observing for a return to (or near to) a baseline level obtained in step ii) after an increase in deoxyhaemoglobin level induced in step iii).

6. The method of claim 1, comprising observing a change in signal in step v) across the entire target region.

7. The method of claim 1, wherein the signal indicative of deoxyhaemoglobin level is a $T_2^*$ signal.

8. The method of claim 1, wherein step iv) comprises obtaining a plurality of measurements over a period of time from about 5 seconds to about 10 minutes.

9. The method of claim 1, comprising taking the baseline measurement before administering the oxygen carrier.

10. The method of claim 1, comprising observing for a temporal-spatial wave of signal change in at least a part of the target region after administering the oxygen carrier.

11. The method of claim 10, comprising observing for a change in a signal indicative of higher levels of deoxyhaemoglobin moving outwardly from an ischaemic core of the animal.

12. The method of claim 1, comprising administering oxygen orally in step i).

13. The method of claim 12, comprising administering the oxygen at a fraction of inspired oxygen ($FiO_2$) above atmospheric oxygen concentrations.

14. The method of claim 1, comprising identifying a penumbra associated with an ischaemic event in the central nervous system.

15. The method of claim 1, comprising identifying an extent of a penumbra following a stroke.

16. The method of claim 1, wherein the animal is a vertebrate.

17. The method of claim 1, wherein the oxygen carrier is a perfluorocarbon (PFC).

18. The method of claim 17, wherein the PFC is FC-75, perflubron, or perfluorodecalin.

19. The method of claim 1, comprising delivering the oxygen carrier as a bolus having a sharply defined start.

20. The method of claim 19, wherein the bolus has a sharply defined end.

21. The method of claim 1, comprising administering a total quantity of oxygen carrier in a range of 1 ml to 3 ml per kg body weight.

22. The method of claim 1, comprising taking a clinical decision based on the measurements, which clinical decision affects the therapeutic treatment of the animal.

23. The method of claim 22, wherein the decision is whether to administer thrombolytic treatment to the animal in the case of an infarction.

24. The method of claim 22, comprising assisting a clinician in deciding on the best course of treatment following a stroke based on the comparison and correlation of step v).

25. The method of claim 1 comprising, when the comparison in step v) reveals that there is little or no penumbra surrounding the animal's ischaemic core, concluding that treatment of the animal by thrombolysis may be undesirable.

26. The method of claim 1 comprising, when the comparison in step v) reveals that there is a clear penumbra surrounding the animal's ischaemic core, concluding that treatment of the animal by thrombolysis may be desirable.

27. A diagnostic method comprising the steps of claim 1 and the further step of deciding, based upon the comparison of step v), on an appropriate course of treatment for the animal.

28. The method of claim 8 in which step iv) comprises obtaining a plurality of measurements over a period of time from 60 seconds to about 5 minutes.

* * * * *